United States Patent
Ansari et al.

(10) Patent No.: US 11,697,626 B2
(45) Date of Patent: Jul. 11, 2023

(54) METHOD OF PRODUCING A FUEL ADDITIVE WITH A HYDRATION UNIT

(71) Applicant: SABIC Global Technologies B.V., Bergen op Zoom (NL)

(72) Inventors: Mohammed Bismillah Ansari, Riyadh (SA); Guillermo Leal, Riyadh (SA); Vijay Dinkar Bodas, Riyadh (SA); Naif Mohammed Al-Naddah Al-Otaibi, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 39 days.

(21) Appl. No.: 17/054,906

(22) PCT Filed: May 6, 2019

(86) PCT No.: PCT/IB2019/053697
§ 371 (c)(1),
(2) Date: Nov. 12, 2020

(87) PCT Pub. No.: WO2019/220257
PCT Pub. Date: Nov. 21, 2019

(65) Prior Publication Data
US 2021/0214290 A1  Jul. 15, 2021

Related U.S. Application Data

(60) Provisional application No. 62/673,289, filed on May 18, 2018.

(51) Int. Cl.
*C07C 5/05* (2006.01)
*C07C 7/08* (2006.01)
(Continued)

(52) U.S. Cl.
CPC .......... *C07C 5/05* (2013.01); *C07C 7/08* (2013.01); *C07C 29/08* (2013.01); *C10G 11/00* (2013.01);
(Continued)

(58) Field of Classification Search
CPC .. C07C 5/05; C07C 29/04; C07C 7/08; C07C 29/08; C07C 7/04; C07C 2523/40;
(Continued)

(56) References Cited

U.S. PATENT DOCUMENTS 3,061,654 A  10/1962  Gensheimer et al.
3,797,690 A  3/1974  Taylor et al.
(Continued)

FOREIGN PATENT DOCUMENTS

CA  2018524 A1  12/1990
CN  1044804 C  8/1999
(Continued)

OTHER PUBLICATIONS

Bender et al.; "Selective Hydrogenation in Steam Cracking"; 21st Annual Saudi-Japan Symposium; Catalysts in Petroleum Refining & Petrochemicals; King Fahd University of Petroleum & Minerals; 2011; Abstract only; pp. 1-3.
(Continued)

*Primary Examiner* — Thuan D Dang
(74) *Attorney, Agent, or Firm* — Cantor Colburn LLP (57) ABSTRACT

A method of producing a fuel additive includes: passing a raffinate stream comprising C4 hydrocarbons through a hydrogenation unit, forming a first process stream; passing the first process stream through an extractive distillation unit, forming a C4 olefin stream; passing the C4 olefin stream through a stripper column, forming a purified C4 olefin stream; and forming the fuel additive by passing the purified C4 olefin stream through a hydration unit.

18 Claims, 1 Drawing Sheet

(51) Int. Cl.
  *C07C 29/08* (2006.01)
  *C10G 11/00* (2006.01)
  *C10L 1/16* (2006.01)
(52) U.S. Cl.
  CPC ..... *C10L 1/1608* (2013.01); *C10L 2200/0423* (2013.01); *C10L 2230/22* (2013.01)
(58) Field of Classification Search
  CPC ............. C07C 2523/72; C07C 2523/74; C10L 1/1608; C10L 2200/0423; C10L 2230/22; C10G 11/00; C10G 45/32; C10G 50/00
  See application file for complete search history.

(56) References Cited

U.S. PATENT DOCUMENTS

| | | |
|---|---|---|
| 3,849,082 A | 11/1974 | Kozlowski et al. |
| 3,912,463 A * | 10/1975 | Kozlowski ............. C10L 1/023 44/446 |
| 4,267,397 A | 5/1981 | Schmidt et al. |
| 4,324,936 A | 4/1982 | Mikulicz |
| 4,334,890 A | 6/1982 | Kochar et al. |
| 4,336,046 A | 6/1982 | Schorre et al. |
| 4,356,339 A | 10/1982 | Imaizumi et al. |
| 4,408,085 A | 10/1983 | Gottlieb et al. |
| 4,423,251 A | 12/1983 | Pujado et al. |
| 4,436,946 A | 3/1984 | Smitny |
| 4,455,445 A | 6/1984 | Neuzil et al. |
| 4,499,313 A | 2/1985 | Okumura et al. |
| 4,540,831 A | 9/1985 | Briggs |
| 4,754,078 A | 6/1988 | Vora et al. |
| 4,773,968 A | 9/1988 | O'Connell et al. |
| 4,783,555 A | 11/1988 | Atkins |
| 4,797,133 A | 1/1989 | Pujado |
| 4,927,977 A | 5/1990 | Child et al. |
| 5,227,553 A | 7/1993 | Polanek et al. |
| 5,254,748 A | 10/1993 | Hensley et al. |
| 5,382,707 A | 1/1995 | Rubin et al. |
| 5,523,502 A | 6/1996 | Rubin |
| 5,563,299 A | 10/1996 | Paludetto et al. |
| 5,628,880 A | 5/1997 | Hearn et al. |
| 5,672,795 A | 9/1997 | Vora et al. |
| 5,864,052 A | 1/1999 | Nierlich et al. |
| 5,877,365 A | 3/1999 | Chodorge et al. |
| 5,898,091 A | 4/1999 | Chodorge et al. |
| 5,955,640 A | 9/1999 | Paludetto et al. |
| 6,580,009 B2 | 6/2003 | Schwab et al. |
| 7,227,047 B2 | 6/2007 | Risch et al. |
| 7,459,593 B1 | 12/2008 | Krupa et al. |
| 7,462,277 B2 | 12/2008 | Adrian et al. |
| 7,473,812 B2 | 1/2009 | Peters et al. |
| 7,485,761 B2 | 2/2009 | Schindler et al. |
| 8,124,572 B2 | 2/2012 | Miller |
| 8,395,007 B2 | 3/2013 | Wright et al. |
| 8,999,013 B2 | 4/2015 | Xu et al. |
| 9,187,388 B2 | 11/2015 | Arjah et al. |
| 9,611,192 B2 | 4/2017 | Digiulio |
| 10,774,020 B2 | 9/2020 | Di Girolamo et al. |
| 2002/0169346 A1 | 11/2002 | Commereuc et al. |
| 2003/0158429 A1 | 8/2003 | Albiez et al. |
| 2004/0171891 A1 | 9/2004 | Scholz et al. |
| 2005/0107628 A1 | 5/2005 | Roper et al. |
| 2005/0288534 A1 | 12/2005 | Fernandez et al. |
| 2007/0149839 A1 | 6/2007 | Rix et al. |
| 2007/0265483 A1 | 11/2007 | Himelfarb |
| 2008/0146858 A1 | 6/2008 | Elomari et al. |
| 2008/0312481 A1 | 12/2008 | Leyshon |
| 2009/0193710 A1 | 8/2009 | Xiong et al. |
| 2011/0040133 A1 | 2/2011 | Vermeiren et al. |
| 2011/0230632 A1 | 9/2011 | Abhari |
| 2012/0117862 A1 | 5/2012 | Xu |
| 2012/0283492 A1 | 11/2012 | Dalemat et al. |
| 2013/0072732 A1 | 3/2013 | Breuil et al. |
| 2013/0104449 A1 | 5/2013 | Xu et al. |
| 2013/0172627 A1 * | 7/2013 | Chewter .................. C10G 7/08 585/303 |
| 2013/0331620 A1 | 12/2013 | Abhari |
| 2014/0039226 A1 | 2/2014 | Xu et al. |
| 2014/0142350 A1 | 5/2014 | Weiner et al. |
| 2015/0225320 A1 | 8/2015 | Shaik et al. |
| 2015/0322181 A1 | 11/2015 | Kim et al. |
| 2016/0326079 A1 | 11/2016 | Lee et al. |
| 2017/0073289 A1 | 3/2017 | Leal et al. |
| 2017/0198231 A1 | 7/2017 | Xu et al. |
| 2017/0253540 A1 | 9/2017 | Hofel et al. |
| 2020/0157450 A1 | 5/2020 | Leal et al. |
| 2021/0002185 A1 | 1/2021 | Leal et al. |
| 2021/0024837 A1 | 1/2021 | Leal et al. |
| 2021/0024843 A1 | 1/2021 | Leal et al. |
| 2021/0155862 A1 | 5/2021 | Leal et al. |
| 2021/0171848 A1 | 6/2021 | Leal et al. |
| 2021/0246088 A1 | 8/2021 | Leal et al. |

FOREIGN PATENT DOCUMENTS

| | | |
|---|---|---|
| CN | 1506344 A | 6/2004 |
| CN | 1736589 A | 2/2006 |
| CN | 101279879 A | 10/2008 |
| CN | 102070391 A | 5/2011 |
| CN | 105585411 A | 5/2016 |
| CN | 106608791 A | 5/2017 |
| CN | 102372573 A | 3/2021 |
| EP | 0063813 B1 | 11/1982 |
| EP | 0102840 B1 | 3/1984 |
| EP | 0253679 | 1/1988 |
| EP | 0605822 A1 | 7/1994 |
| GB | 1374368 | 11/1974 |
| JP | S5920232 A | 2/1984 |
| JP | 2010111596 A | 5/2010 |
| RU | 2470905 C1 | 12/2012 |
| WO | 9011268 | 10/1990 |
| WO | 9732838 A1 | 9/1997 |
| WO | 0043336 A1 | 7/2000 |
| WO | 0146095 A1 | 6/2001 |
| WO | 2006113191 A2 | 10/2006 |
| WO | 2007024733 A2 | 3/2007 |
| WO | 2012095744 A2 | 7/2012 |
| WO | 2013104692 A1 | 7/2013 |
| WO | 2014153570 A2 | 9/2014 |
| WO | 2014160825 A1 | 10/2014 |
| WO | 2015089005 A1 | 6/2015 |
| WO | 2015123026 A1 | 8/2015 |
| WO | 2019207477 A1 | 10/2019 |

OTHER PUBLICATIONS

Brockwell et al.; "Synthesize ethers"; Hydrocarbon Processing, vol. 70, No. 9; 1991; pp. 133-141.
International Search Report for International Application No. PCT/IB2019/052177; International Filing Date Mar. 18, 2019; dated Jun. 26, 2019; 3 pages.
International Search Report for International Application No. PCT/IB2019/052178; International Filing Date Mar. 18, 2019; dated Jun. 26, 2019; 6 pages.
International Search Report for International Application No. PCT/IB2019/057784; International Filing Date Sep. 16, 2019; dated Jan. 7, 2020; 5 pages.
International Search Report for International Application No. PCT/US2019/026985; International Filing Date Apr. 11, 2019; dated May 27, 2019; 6 pages.
International Search Report for International Application No. PCT/US2019/028092; International Filing Date Apr. 18, 2019; dated Jun. 26, 2019; 6 pages.
International Search Report for International Application No. PCT/US2019/028099; International Filing Date Apr. 18, 2019; dated Jun. 26, 2019; 6 pages.
International Search Report; International Application No. PCT/IB2018/055647; International Filing Date: Jul. 27, 2018; dated Oct. 30, 2018; 6 pages.
Izquierdo et al.; "Equilibrium Constants for Methyl tert-Butyl Ether Liquid-Phas Synthesis"; J. Chem. Eng. Data, vol. 37; 1992; pp. 339-343.

(56) References Cited

OTHER PUBLICATIONS

Kalamaras et al.; "SuperButol—A novel high-octane gasoline blending component"; Fuel, vol. 195; 2017; pp. 165-173.
Streich et al.; "Secure the Best Benefits from C4 Hydrocarbon Processing—Part 1: Separation Sequences" Hydrocarbon Processing: Process Engineering and Optimization; 2016; 6 pages.
Written Opinion for International Application No. PCT/IB2019/052177; International Filing Date Mar. 18, 2019; dated Jun. 26, 2019; 9 pages.
Written Opinion for International Application No. PCT/IB2019/052178; International Filing Date Mar. 18, 2019; dated Jun. 26, 2019; 9 pages.
Written Opinion for International Application No. PCT/IB2019/057784; International Filing Date Sep. 16, 2019; dated Jan. 7, 2020; 7 pages.
Written Opinion for International Application No. PCT/US2019/026985; International Filing Date Apr. 11, 2019; dated May 27, 2019; 7 pages.
Written Opinion for International Application No. PCT/US2019/028092; International Filing Date Apr. 18, 2019; dated Jun. 26, 2019; 9 pages.
Written Opinion for International Application No. PCT/US2019/028099; International Filing Date Apr. 18, 2019; dated Jun. 26, 2019; 13 pages.
Written Opinion; International Application No. PCT/IB2018/055647; International Filing Date: Jul. 27, 2018; dated Oct. 30, 2018; 11 pages.
Bodas et al.; U.S. Appl. No. 17/292,261; entitled "Process and System for Producing Ethylene and at Least One of Butanol and an Alkyl Tert-Butyl Ether"; filed with USPTO filed May 7, 2021.
International Search Report for International Application No. PCT/IB2020/051908; International Filing Date Mar. 5, 2020; dated May 29, 2020; 6 pages.
Leal et al. U.S. Appl. No. 17/436,753, entitled "Method of Producing a Fuel Additive", filed with the USPTO filed Sep. 7, 2021.
Written Opinion for International Application No. PCT/IB2020/051908; International Filing Date Mar. 5, 2020; dated May 29, 2020; 9 pages.
International Search Report for International Application No. PCT/IB2019/059984; International Filing Date Nov. 20, 2019; dated Feb. 21, 2020; 5 pages.
Written Opinion for International Application No. PCT/IB2019/059984; International Filing Date Nov. 20, 2019; dated Feb. 21, 2020; 8 pages.
International Search Report for International Application No. PCT/IB2019/053697; International Filing Date May 6, 2019; dated Aug. 28, 2019; 11 pages.
Written Opinion for International Application No. PCT/IB2019/053697; International Filing Date May 6, 2019; dated Aug. 28, 2019; 9 pages.
Fuel Additives Selection Guide: Types, Features, Applications, Engineering 360, 4 pages, obtained May 11, 2022, http://www.globalspec.com/learnmore/materials_chemicals_adhesives/industrial_oils_fluids/fuel_oil_fluid_additives (Year: 2022).
Hua et al.; "Molecular Sieve-Catalyzed Mixed C Hydration"; Petrochemical Technology, vol. 34 Supplement; 2005; pp. 156-158.
Tianpu; "C3 and C4 Hydration Technology"; Qilu Petrochemical Technology, vol. 29, No. 3; 2001; pp. 218-223.
Zhiping et al.; "Discussion on Production Process Route of 1-Butene Products"; Chemical Industry and Engineering; 2003; pp. 178-184.
"Organic Chemistry"; Edited by Compilation Group of Chemistry Textbooks for Vocational and Technical Colleges; Higher Education Press; 2000; p. 66.
Ma Shichang et al.; "Dictionary of Chemical Substances"; Shaanxi Science and Technology Institute; 1999; p. 101.

\* cited by examiner

METHOD OF PRODUCING A FUEL ADDITIVE WITH A HYDRATION UNIT

CROSS REFERENCE TO RELATED APPLICATIONS

This application is a National Stage application of PCT/IB2019/053697, filed May 6, 2019, which is incorporated herein by reference in its entirety, and which claims the benefit of U.S. Provisional Application No. 62/673,289, filed May 18, 2018.

BACKGROUND

Commercial gasoline, which is fuel for internal combustion engines, is a refined petroleum product that is typically a mixture of hydrocarbons (base gasoline), additives, and blending agents. Additives and blending agents, for example octane boosters, are added to the base gasoline to enhance the performance and the stability of gasoline.

When used in high compression internal combustion engines, gasoline has the tendency to "knock." Knocking occurs when combustion of the air/fuel mixture in the cylinder does not start off correctly in response to ignition because one or more pockets of air/fuel mixture pre-ignite outside the envelope of the normal combustion front. Anti-knocking agents, also known as octane boosters, reduce the engine knocking phenomenon, and increase the octane rating of the gasoline.

Hydrocarbon cracking processes are important conversion processes used in petroleum refineries. For example, fluid catalytic cracking (FCC) is widely used to convert the high-boiling, high-molecular weight hydrocarbon fractions of petroleum crude oils to more valuable gasoline, olefinic gases, and other products. Thermal cracking of naphtha and gas oil is also widely used in the petrochemical industry to produce a variety of olefins and aromatics. For example, hydrocarbon feed stocks can be mixed with steam and subjected to elevated temperatures (e.g., 700-900° C.) in a steam cracker furnace wherein the feed stock components are cracked into various fractions. The effluent of the steam cracker can contain a gaseous mixture of hydrocarbons, for example, saturated and unsaturated olefins and aromatics (C1-C35). The effluent can then be separated into individual olefins (for example, ethylene, propylene, and C4's) and pyrolysis gasoline. Recycle streams of crude hydrocarbons are often formed as byproducts during these cracking processes.

The presence of isobutylene, butadiene, 1-butene, 2-butene, and other components within the crude hydrocarbon streams can allow the formation of valuable alcohols and fuel additives. However, the conversion of crude hydrocarbon streams to fuel additive products can often be inefficient and costly. Furthermore, the final product specifications for such alcohols can be undesirable and can fail to meet market quality requirements. For example, alcohol products can have high levels of impurities, high Reid vapor pressures, e.g., greater than 2.0 pounds per square inch (psi) (greater than 10 kiloPascals, greater than 12 kiloPascals, greater than 13 kiloPascals, greater than 14 kiloPascals), and low octane numbers (e.g., 82 Research Octane Number (RON)), all of which correlate with poor product quality. Any improvement in these specifications and/or the efficiency of the process can provide a more valuable fuel additive product.

Thus, there is a need for an efficient method of producing fuel additives that can make use of crude hydrocarbon streams and produce final products with low impurities and high performance specifications.

SUMMARY

Disclosed, in various embodiments, are methods of producing fuel additives with a hydration unit.

A method of producing a fuel additive, comprises: passing a raffinate stream comprising C4 hydrocarbons through a hydrogenation unit, forming a first process stream; passing the first process stream through an extractive distillation unit, forming a C4 olefin stream; passing the C4 olefin stream through a stripper column, forming a purified C4 olefin stream; and forming the fuel additive product by passing the purified C4 olefin stream through a hydration unit.

A method of producing a fuel additive, comprises: passing a raffinate stream comprising C4 hydrocarbons through a hydrogenation unit, forming a first process stream, wherein greater than or equal to 90% by weight of any butadiene present in the raffinate stream is converted to 1-butene and/or 2-butene within the hydrogenation unit; passing the first process stream and a solvent comprising N-methylpyrrolidone, formylpyrrolidine, N-formylmorpholine, butyrolactone, or a combination thereof through an extractive distillation unit, producing a C4 olefin stream; passing the C4 olefin stream through a stripper column, producing a purified C4 olefin stream; passing the purified C4 olefin stream through a hydration unit, wherein the purified C4 olefin stream is exposed to an acid catalyst comprising phosphoric acid, cation exchange resin, sulphonated polystyrene, hypophosphorous acid, polymer, niobium oxide, zeolite, or a combination thereof in the hydration unit; and withdrawing a C4 alcohol fuel additive product from the hydration unit, wherein the fuel additive product comprises 0.01% to 50% by weight trimethyl-pentane.

These and other features and characteristics are more particularly described below.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

The FIGURE is a schematic diagram representing a unit sequence for producing fuel additives.

DETAILED DESCRIPTION

Disclosed herein is an efficient process for producing fuel additive products, such as C4 alcohols. The process is able to convert a catalyst poisoning agent such as butadiene present in the feedstream to butene for use in forming the fuel additive products. Additionally, separation of paraffins from the feedstream can allow for additional C4 synthesis, reducing waste, thereby increasing economic and financial benefits of the claimed efficient process and products derived therefrom. The methods disclosed herein can make use of crude hydrocarbon streams and produce final products with low impurities and high performance specifications. For example, the methods disclosed herein can provide a sequence of operations that converts crude hydrocarbons into valuable fuel additives, such as alcohol fuel additives (e.g., C4 alcohols). The methods can significantly improve the efficiency of the process, not only reducing total capital costs, but also assisting in maximizing the financial benefits of converting impurities or poisonous material to the process in the feedstream to valuable products, i.e., fuel additive products. The final fuel additive products can comprise 1-butanol, 2-butanol, tert-butyl alcohol, C4-dimer, ethers such as di-isobutyl ether, di-sec-butyl ether, or a combination comprising at least one of the forgoing, for example, the final fuel additive products can have levels of the C4-dimer comprising trimethyl-pentane, di-isobutylene, 2,2,4 trimethyl-pentane, 2,3,3 trimethyl-pentane, or a combination thereof in an amount of 0.01% by weight to 50% by weight, based on the total weight of the fuel additive product, high octane numbers (e.g., greater than or equal to 85 RON, or greater than or equal to 87 RON), and low Reid vapor pressures of less than or equal to 55 kiloPascals (8.0 pounds per square inch (psi)). For example, the trimethyl-pentane can be present in an amount of 0.1 to 25% by weight, for example, 1 to 20% by weight. Any one or all of these properties can correlate with high performance and high market value. The methods disclosed herein can also produce secondary products along with the fuel additive product. For example, ethylene and propylene products can be produced (for example, via recycle streams to the cracker) along with the fuel additive product, thus maximizing the efficiency and productivity of the process.

The methods disclosed herein can provide a process for producing a fuel additive with a minimal number of components. For example, the inclusion of a hydrogenation unit, for example, a selective hydrogenation unit, in the methods can transform the butadiene components present in the feedstream to 1-butene and/or 2-butene (e.g., cis-2-butene, trans-2-butene, or a combination thereof) together with the separation of olefins and paraffins present in the outlet steam from the hydrogenation unit by distillation (e.g., extractive distillation). A fuel additive product can then be produced by hydration of the olefins (e.g., C4 olefins) wherein the fuel additive product can comprise mixed alcohols, such as C4 alcohols. The paraffin stream, e.g., a C4 paraffin stream, from the distillation unit can be sent to a methyl tertiary butyl ether (MTBE) plant as feedstock for the production of MTBE. The C4 paraffin stream can comprise iso-butane (IC4), n-butane (N—C4), or a combination thereof. The method can produce fuel additive products, for example, alcohol fuel additive products, for example, C4 fuel additive products, from mixed crude hydrocarbon feedstocks, for example, C4 hydrocarbons, from cracking units, such as steam cracking units or fluid catalytic cracking (FCC) units, with minimum capital expenditures and maximum production of the fuel additive product with even further increased efficiency.

The methods disclosed herein can provide a novel design for utilization and transformation of crude hydrocarbons from a cracking unit recycle stream as a feedstock to maximize production of the fuel additive product. The methods include the use of selective hydrogenation units, distillation units, and hydration units for the maximum production of the fuel additive product.

Raffinate streams (e.g., C4 raffinate streams) from a cracking unit such as a steam cracker and/or a fluid catalytic cracker (FCC) can comprise propane, propylene, n-butane, iso-butane, isobutylene, 1-butene, cis-2-butene, trans-2-butene, 1,3-butadiene, or a combination thereof. The total C4 olefin content in the raffinate stream from the steam cracker or the FCC unit can optionally be about 40% by weight of the feedstream (isobutylene, 1-butene, 2-butene, or a combination thereof), with the remainder containing paraffins and butadiene, though amounts may vary from cracker to cracker. Butadiene is an impurity in the process and can be poisonous to catalysts present in the process, such as a hydration catalyst in the hydration unit. Furthermore, the presence of C4 paraffins in the C4 olefin stream in the hydration unit increases the amount of material needing to be recycled by at least three times. This amount of material needing to be recycled can be reduced by separation of paraffins from the C4 olefin stream before it is sent to the hydration unit.

The methods of making a fuel additive product as described herein can include passing a raffinate stream through a first hydrogenation unit. For example, the raffinate stream can include C4 hydrocarbons. The first hydrogenation unit can be a selective hydrogenation unit. This hydrogenation unit can convert the butadiene present in the raffinate stream to 1-butene and 2-butene, forming a first process stream. For example, greater than or equal to 90% by weight of the butadiene present in the raffinate stream can be converted to 1-butene and 2-butene. The first process stream can then be passed through a distillation unit, which can separate the first process stream into component hydrocarbons. The reduction of butadiene and the maximization of butenes in the feedstream can increase desirable product specifications of the fuel additive product, for example, the octane number and Reid vapor pressure. Recycle streams from within the process can be used to produce ethylene and propylene as secondary products, for example via steam cracker, or to produce MTBE, for example via deisobutanizer, isomerization unit, dehydrogenation unit and MTBE synthesis unit. Accordingly, the present process can maximize product quality for a fuel additive product while also producing additional secondary products in an efficient manner.

The methods disclosed herein can include passing a feedstream of crude hydrocarbons through a hydrocarbon cracking unit, for example, a catalytic cracking unit (e.g., FCC) and/or steam cracking unit, to produce a raffinate stream.

The raffinate stream can comprise hydrocarbons, for example, C4 hydrocarbons. The raffinate stream can comprise propane, propylene, 1,3-butadiene, 1,2-butadiene, isobutylene, cis-2-butene, trans-2-butene, 1-butene, isobutane, n-butane, or a combination thereof. A total C4 olefin content (e.g., isobutylene, 1-butene, and/or 2-butene) of the raffinate stream can be greater than or equal to 40% by weight, wherein the raffinate stream can comprise greater than or equal to 0.1% by weight isobutylene. The total C4 olefin content of the raffinate stream when withdrawn from a fluid catalytic cracking unit can be greater than or equal to 35% by weight and the stream can comprise greater than or equal to 30% by weight isobutane and n-butane, for example, isobutylene in an amount of 0.1-25% by weight, olefins in an amount of 30-65% by weight, and saturated hydrocarbons in an amount of 30-65% by weight.

The methods disclosed herein can include passing a raffinate stream through a hydrogenation unit to form a first process stream. The first process stream can be passed through a distillation unit, for example, an extractive distillation unit, to form a C4 olefin stream and a C4 paraffin stream. The C4 olefin stream can be passed through a stripper column. The stripper column can remove solvent from the C4 olefin stream. The C4 olefin stream can be passed through a hydration unit after solvent removal to form the fuel additive. The C4 paraffin stream can be sent to a MTBE synthesis plant and subjected to various downstream processes in order to form MTBE. For example, the C4 paraffin stream can be subjected to a de-isobutanizer column to separate n-butane from iso-butane, an isomerization unit, a dehydrogenation unit, and/or a MTBE synthesis unit.

Butadiene present in the raffinate stream can be converted to 1-butene and/or 2-butene (e.g., cis-2-butene, trans-2-butene), or a combination thereof in the hydrogenation unit, for example, a selective hydrogenation unit. In the distillation column, the first process stream can be separated into the C4 olefin stream and a C4 paraffin stream. The C4 paraffin stream can be fed to a MTBE synthesis plant for the production of MTBE.

The hydrogenation unit, which can be a selective hydrogenation unit, can selectively convert butadiene to 1-butene and 2-butene (i.e., cis-2-butene, trans-2-butene, or a combination comprising least one of the foregoing). The raffinate stream entering the hydrogenation unit can comprise less than or equal to 50% by weight butadiene, for example, less than or equal to 30% by weight butadiene, for example, less than or equal to 42% by weight butadiene. The conversion rate of butadiene to 1-butene, cis-2-butene, and trans-2-butene can be greater than or equal to 50%, for example, greater than or equal to 85%, for example, greater than or equal to 90%, for example, greater than or equal to 95%. The hydrogenation unit can also convert propylene, methyl acetylene, and propadiene present in the process stream to their corresponding alkanes or alkenes. Hydrogen can be added to the process stream prior to passing through the first hydrogenation unit.

The hydrogenation unit can comprise multiple reactors in series, for example, the unit can comprise three reactor stages. The first two reactor stages can convert butadiene present in the feedstream to 1-butene and 2-butene. The first two reactor stages can comprise a selective hydrogenation catalyst. For example, the hydrogenation catalyst can comprise palladium with an aluminum base. The hydrogenation catalyst can comprise platinum, rhodium, palladium, ruthenium, cobalt, nickel, copper, or a combination thereof. The catalyst can be the same for the first two reactor stages. Hydrogen can be injected into the feedstream prior to passing through the first reactor stage.

Final hydrogenation of di-olefins to a desired product of mono-olefins can be achieved in the third reactor stage. Carbon monoxide can be injected into the third reactor stage to attenuate the catalyst and minimize the isomerization reaction from 1-butene to 2-butene. During normal operations, the desired carbon monoxide injection rate can be 2 parts per million of the feedstream to the third reactor stage. The rate can be increased if too much 1-butene is being lost to 2-butene. A first process stream can then be withdrawn from the hydrogenation unit. Operation conditions for the selective hydrogenation unit are shown in Table 1. Temperature is reported in degrees Celsius and pressure in pounds per square inch gage (psig) and kiloPascals (kPa).

TABLE 1

| Reactor | Temp °C. | Pressure (psig) | Catalyst | Representative BD content at exit |
|---|---|---|---|---|
| 1st Reactor | 40-70 | 140-400 (965-2758 kPa) | Noble metal/Alumina | 7% |
| 2nd Reactor | 50-60 | 140-400 (965-2758 kPa) | Noble metal/Alumina | 1% |
| 3rd Reactor | 60-80 | 250-270 (1724-1862 kPa) | Noble metal/Alumina | <0.01% |

The first process stream can then be passed through a distillation unit, for example, an extractive distillation unit. An overhead pressure in the distillation unit can be 600 to 1000 kPa and a reflux temperature can be 35-50° C. This distillation unit can separate the first process stream into component hydrocarbons. For example, paraffins and olefins can be separated in the distillation unit. A temperature within the distillation unit can be 20° C. to 150° C., for example, 40° C. to 140° C. A pressure within the distillation unit can be 300 kiloPascals to 1500 kiloPascals, for example, 310 kiloPascals to 1000 kiloPascals, for example, 350 kiloPascals to 800 kiloPascals.

This distillation unit can comprise an extractive distillation column, followed by solvent degassing, solvent regeneration, and solvent recovery. The extractive distillation unit can comprise a solvent comprising hydrogenated heterocyclic compounds with 5 to 6 members, preferably, wherein the solvent further comprises nitrogen, oxygen, a carbonyl group, or a combination thereof. For example, the solvent can comprise compounds selected from morpholine derivatives and/or pyrrolidone derivatives, one or more aromatic or aliphatic solvents, preferably toluene, benzene, ethylbenzene, cumene, xylenes, mesitylene, hexane, octane, cyclohexane, olefins (preferably, hexene, heptane, octane), or ethers (preferably diethylether, tetrahydrofuran), dimethylformamide, n-methyl-pyrrolidine, formylpyrrolidine, N-formylmorpholine, butyrolactone, acetonitrile, furfural, N-methyl-2-pyrrolidone, acetone, dimethylacetamide, cuprous ammonium acetate or β-methoxypropionitrile, more preferably an aromatic solvent, most preferably n-formylmorpholine can be used as the solvent.

A C4 olefin stream withdrawn from the distillation unit can be passed through a stripper column. The C4 olefin stream can comprise 1-butene, 2-butene, or a combination thereof. The 2-butene component can comprise cis-2-butene, trans-2-butene, or a combination thereof. The stripper column can remove solvent from the C4 olefin stream. The solvent (as well as any associated impurities) can be recycled to the distillation unit as a regenerated recycle solvent stream. A temperature within the stripper column can be 20° C. to 200° C., for example, 30° C. to 170° C. A pressure within the stripper column can be 300 kiloPascals to 1500 kiloPascals, for example, 350 kiloPascals to 1200 kiloPascals, for example, 400 kiloPascals to 700 kiloPascals.

The hydration unit can hydrate the C4 olefin stream to produce a fuel additive product, for example, an alcohol fuel additive product, for example, a mixed alcohols fuel additive product, for example, a C4 alcohol fuel additive product. The C4 olefin stream can comprise 1-butene, 2-butene, or a combination thereof wherein cis-2-butene, trans-butene, or a combination thereof can be present in the 2-butene component of the C4 olefin stream. The C4 olefin stream entering the hydration unit can comprise less than or equal to 5% butadiene by weight, for example, less than or equal to 3% butadiene by weight, for example, less than or equal to 1% butadiene by weight. The fuel additive product can be withdrawn from the hydration unit via a product stream. Water can be fed to the hydration unit via a water stream. The hydration unit can comprise an oscillating baffle reactor, a fixed bed reactor, a membrane integrated reactor, isothermal multitubular reactor, or a combination thereof. The hydration reactor can comprise multiple reactors operating either in series or parallel. When multiple reactors are present, a first reactor can operate at a lower temperature than a second reactor.

The hydration unit can convert C4 olefins into C4 alcohols over acid catalysts (e.g., phosphoric acid, AMBERLYST, resin/sulfonated polystyrene/HPA/polymer supported niobium oxide, as well as zeolite supported acid catalyst).

For example, the hydration unit can convert butene present in the C4 olefin stream to butanol. For example, 0.10-99% by weight of the butene present in the C4 olefin stream can be converted to butanol within the hydration unit, for example greater than or equal to 0.10% by weight, for example, greater than or equal to 80% by weight. The C4 olefin stream can be contacted with water and a catalyst within the hydration unit. For example, the catalyst can comprise an acid catalyst comprising phosphoric acid, a cation exchange resin, sulphonated polystyrene, hypophosphorous acid, polymer, niobium oxide, zeolite, or a combination thereof. Water and butene can be present within the hydration unit in a molar ratio of 1.0-1000 mole of water to 1 mole of butene, for example, 10 moles of water to 1 mole of butene. A temperature within the hydration unit can be 30° C. to 250° C., for example, 100° C. to 200° C. A pressure within the hydration unit can be 500 kiloPascals to 20,000 kiloPascals, for example, 500 kiloPascals to 10,000 kiloPascals, for example, 7500 kiloPascals. The hydration reactors, if in series, can be operated at two different temperature levels. The first reactor can be operated at lower temperature (preferably below 70° C. at the exit of reactor) and the second reactor can operate at a temperature of up to 250° C.

The fuel additive product can comprise 1-butanol, 2-butanol, tert-butyl alcohol, di-isobutene, C4-dimer, ethers such as di-isobutyl ether, di-sec-butyl ether, or a combination comprising at least one of the forgoing, for example, the C4-dimer can comprise di-isobutylene, 2,2,4 trimethyl-pentane, 2,3,3 trimethyl-pentane, or a combination thereof. The fuel additive product can comprise greater than or equal to 0.01% by weight, for example, 5% by weight trimethyl-pentane, for example, greater than or equal to 10% by weight, for example, greater than or equal to 15% by weight greater than or equal to 20%, for example, greater than or equal to 50% by weight, for example, 0.01% by weight to 50% by weight trimethyl-pentane. In some embodiments, the alcohols can be present in an amount ranging from 70% by weight to 100% by weight alcohols, with the remainder comprising ethers, C4 dimers, or a combination thereof. An octane number of the fuel additive product can be greater than or equal to 80 according to the Anti-Knock Index, for example, greater than or equal to 85, for example, greater than or equal to 87, for example, greater than or equal to 90, for example, greater than or equal to 93 for example, greater than or equal to 95.

The octane number is a standard measurement used to gauge the performance of an engine or fuel. The higher the octane number, the more compression the fuel is able to withstand before igniting. Fuels with higher octane ratings are generally used in high performance gasoline engines that need higher compression ratios. Fuels with lower octane numbers can be desirable for diesel engines because diesel engines do not compress the fuel, but rather compress only air and then inject fuel into the air which is heated by compression. Gasoline engines rely on ignition of air and fuel compressed together as a mixture, which is ignited at the end of the compression stroke using spark plugs. As a result, high compressibility of fuel is a consideration for gasoline engines.

The Anti-Knock Index is measured by adding the research octane number and the motor octane number and dividing by two, i.e., (RON+MON)/2. The Research Octane Number is determined by running the fuel in a test engine at a speed of 600 revolutions per minute with a variable compression ratio under controlled conditions, and comparing the results with those for mixtures of iso-octane and n-heptane. Motor Octane Number is determined by testing a similar test engine to that used in determining the Research Octane Number but at a speed of 900 revolutions per minute with a preheated fuel mixture, higher engine speed, and variable ignition timing. Depending on the composition, the Motor Octane Number can be about 8 to 12 octane numbers lower than the Research Octane Number. The research octane number can be greater than or equal to 88, for example, greater than or equal to 91, for example, greater than or equal to 93, for example, greater than equal 95, for example, greater than equal to 100. The motor octane number can be greater than or equal to 82, for example, greater than or equal to 89, for example, greater than or equal to 90, for example, greater than or equal to 93. Higher octane ratings can give higher amounts of energy needed to initiate combustion. Fuels with higher octane ratings are less prone to auto-ignition and can withstand a greater rise in temperature during the compression stroke of an internal combustion engine without auto-igniting.

Reid vapor pressure is used to measure the volatility of gasoline defined as the absolute vapor pressure exerted by a liquid at 37.8° C. as determined by ASTM D-323. This test method measures the vapor pressure of gasoline volatile crude oil, and other volatile petroleum products, except for liquefied petroleum gases. Reid vapor pressure is measured in kiloPascals and represents a relative pressure to atmospheric pressure since ASTM D-323 measures the gage pressure of the sample in a non-evacuated chamber. High levels of vaporization are desired for winter starting and operation and lower levels are desirable in avoiding vapor lock during summer heat. Fuel cannot be pumped when vapor is present in the fuel line and winter starting will be difficult when liquid gasoline in the combustion chambers has not vaporized. This means that the Reid vapor pressure is changed accordingly by oil producers seasonally to maintain gasoline engine reliability.

The Reid vapor pressure of the fuel additive product can be less than or equal to 55.16 kiloPascals, for example, 5 kiloPascals to 55 kiloPascals, for example, 5 kiloPascals to 40 kiloPascals. The Reid vapor pressure can vary during winter and summer conditions such that the pressure can be at the higher end of the values during the winter and at the lower end of the values during the summer.

The C4 paraffin stream can comprise n-butane and iso-butane. The C4 paraffin stream can be withdrawn from the distillation unit and sent to an MTBE synthesis plant. In such a process, the C4 paraffin stream can be subjected to a de-isobutanizer column (DIB), an isomerization unit, a dehydrogenation unit, and a MTBE synthesis unit in order to produce MTBE. Methanol and isobutylene can be present within the MTBE synthesis unit in a molar ratio of 1.0 mole of isobutylene to 0.05 moles to 10.0 moles of methanol, for example, one mole of isobutylene to 0.1 moles to 5.0 moles of methanol, for example, one mole of isobutylene to 0.5 moles to 2.0 moles of methanol. The MTBE product can be withdrawn from the MTBE unit via a MTBE product stream. The purity of the MTBE product can be greater than or equal to 95%. The conversion rate from isobutylene to MTBE within the MTBE unit can be greater than or equal to 75%, for example, greater than or equal to 85%, for example, greater than or equal to 95%. A temperature within the MTBE unit can be 15° C. to 150° C., for example, 35° C. to 125° C. A pressure within the MTBE unit can be 500 kiloPascals to 2800 kiloPascals, for example, 1000 kiloPascals to 2000 kiloPascals, for example, 1500 kiloPascals.

A recycle stream, e.g., a hydrocarbon recycle stream, can be withdrawn from the extractive distillation unit and recycled to a steam cracker unit and/or the initial feed stream. The recycle stream can comprise primarily isobutane, n-butane and traces of 1-butene, 2-butene, or isobutylene or a combination thereof. The recycle stream can optionally be passed through a drying unit for trace water removal and a recycle hydrogenation unit prior to returning to the initial feed stream. The recycle hydrogenation unit can convert the 1-butene, 2-butene and isobutylene present in the recycle stream to n-butane and isobutane. For example, greater than or equal to 90% of any butene present in the hydrocarbon recycle stream can be converted to butane within the recycle hydrogenation unit.

A more complete understanding of the components, processes, and apparatuses disclosed herein can be obtained by reference to the accompanying drawings. These FIGURES (also referred to herein as "FIG.") are merely schematic representations based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description, it is to be understood that like numeric designations refer to components of like function.

Referring now to the FIGURE this simplified schematic diagram represents a unit sequence 10 used in a method for producing fuel additive products. The methods illustrated by unit sequence 10 can include passing a raffinate stream 12 comprising C4 hydrocarbons through a hydrogenation unit 14, forming a first process stream 16. The hydrogenation unit 14 can be a selective hydrogenation unit. Hydrogenation of butadiene present in the raffinate stream 12 occurs in the hydrogenation unit 14. Optionally, a gaseous stream 18, e.g., gaseous $H_2$, can be fed to the hydrogenation unit 14 together with the feedstream 12.

The first process stream 16 can be passed through a heat exchanger 20 and a first portion 28 of the first process stream 16 can be fed to a middle portion 26 of a distillation unit 22, for example, an extractive distillation unit, and a solvent stream 30 can be fed to a top portion 24 of the distillation unit 22. A C4 olefin stream 32 can be withdrawn from a bottom portion 37 of the distillation unit 22 and sent to a stripper column 34. Regenerated solvent can leave the stripper column 34 through regenerated recycle solvent stream 35 and be sent back to the heat exchanger 20. A purified C4 olefin stream 39 is removed from the stripper column 34 and passed through a heat exchanger 36 and a pressure vessel 38 before being passed through an olefin hydration unit 42 to form a crude fuel additive product 44.

The hydration unit 42 can hydrate the purified C4 olefin stream 39 to produce the crude fuel additive product 44, for example, an alcohol fuel additive product. The crude fuel additive product 44 can be withdrawn from the hydration unit 42. Water can be fed to the hydration unit via stream 45. The crude fuel additive product 44 can be passed through a purifying unit 46 which can include a high pressure separator and separation unit consisting of two columns: a column for olefin-fuel additive product separation and a column for water/alcohol separation. A purified fuel additive product 48 can be withdrawn from the purifying unit 46. An olefin and water recycle stream 50 can be removed from the purifying unit 46 and sent back to the purified C4 olefin stream 39 to recycle unreacted olefins and water. Optionally, the water can be passed through a deionizer before returning to the olefin hydration unit 42.

A distillate product stream 51 can be removed from the top portion 24 of the distillation unit 22 and passed through a heat exchanger 52 and a pressure vessel 54 to produce a C4 paraffin stream 56 that can be sent to an MTBE synthesis plant for downstream production of MTBE or to a steam cracker.

The following example is merely illustrative of the methods disclosed herein and is not intended to limit the scope hereof.

EXAMPLE

Example 1

Figure 1:
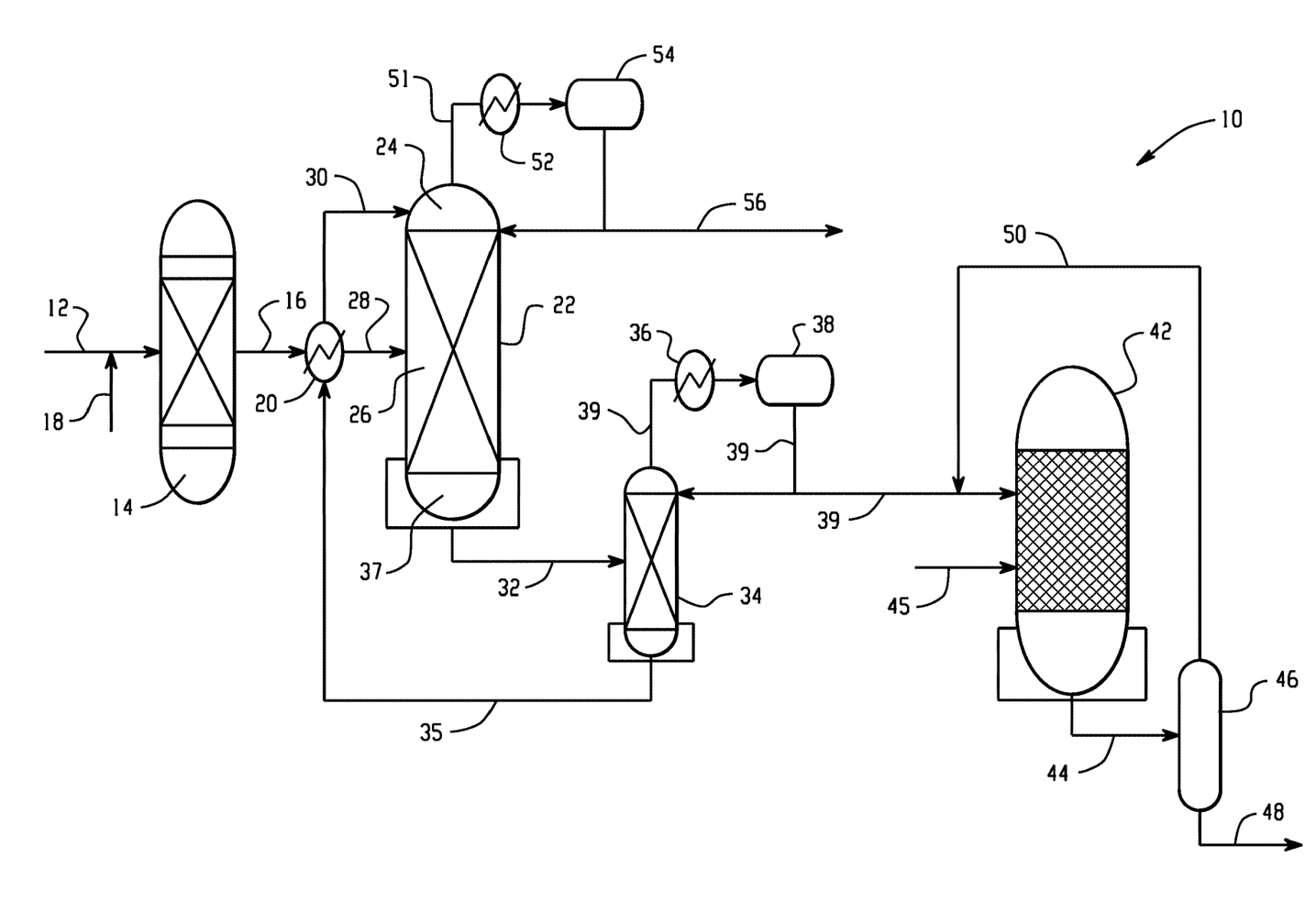

The representative stream compositions for various streams in unit sequence 10 shown in FIG. 1 are listed in Table 2. Stream 1 was equivalent to the raffinate stream 12; Stream 2 corresponded to the first process stream 16; Stream 3 corresponded to the C4 paraffin stream 56; Stream 4 corresponded to the purified C4 olefin stream 39; and Stream 5 corresponded to the purified fuel additive product stream 48. In certain other embodiments, Stream 5 can also comprise C4 dimers. The compositions are given in weight percent. SHU corresponds to the selective hydrogenation unit 14 and hydration corresponds to the hydration unit 42. Mass flow is measured in total weight percent per hour (TPH).

TABLE 2

Composition throughout the process

| | Stream | | | | |
|---|---|---|---|---|---|
| Components | 1 SHU IN | 2 SHU OUT | 3 C4 Paraffins | 4 Hydration IN | 5 Hydration OUT |
| Butadiene | 17.92 | 0.00 | 0.00 | 0.00 | 0.00 |
| 1-butene | 7.54 | 19.11 | 0.00 | 39.25 | 0.00 |
| 2-butene | 5.16 | 10.10 | 0.00 | 20.76 | 0.00 |
| iso-butylene | 19.61 | 19.47 | 0.00 | 39.99 | 0.00 |
| n-butane | 34.58 | 36.24 | 70.60 | 0.00 | 0.00 |
| iso-butane | 15.2 | 15.09 | 29.40 | 0.00 | 0.00 |
| 2-butanol | 0.00 | 0.00 | 0.00 | 0.00 | 60.01 |
| tert-butanol | 0.00 | 0.00 | 0.00 | 0.00 | 39.99 |
| Mass Flow | 75.74 | 76.3 | 39.16 | 37.14 | 49.07 |

As can be seen from Table 2, butadiene present in the raffinate stream is converted mainly to 1-butene and 2-butene within the hydrogenation unit, such that the first process stream is substantially free of butadiene. Substantially free of butadiene as described herein generally refers an amount of butadiene present of 0.1 to 500 parts per million (ppm). Further, as can be seen the stream exiting the hydration unit (Hydration OUT), the fuel additive product comprises 100% by weight alcohols.

Example 2

In this example, a trial was conducted using a single hydration reactor. To mimic a configuration having multiple hydration reactors in series, the reactor product was recycled back through the reactor at specified ratios. In this example, Stream 1 corresponded to the raffinate stream 12; Stream 2 corresponded to the first process stream 16; Stream 3 corresponded to the C4 paraffin stream 56; Stream 4 corresponded to the purified C4 olefin stream 39; and Stream 5 corresponded to the purified fuel additive product stream 48. The compositions are given in weight percent. SHU corresponds to the selective hydrogenation unit 14 and hydration corresponds to the hydration unit 42. Mass flow is measured in total weight percent per hour (TPH).

TABLE 3

Composition throughout the process (recycle/feed ratio: 6:1 (mass:mass))

| | Stream | | | | |
|---|---|---|---|---|---|
| | 1 | 2 | 3 | 4 | 5 |
| Components | SHU IN | SHU OUT | C4 Paraffins | Hydration IN | Hydration OUT |
| Butadiene | 17.9 | 0.0 | 0.0 | 0.0 | 0.0 |
| 1-butene | 7.5 | 19.1 | 0.0 | 39.3 | 0.0 |
| 2-butene | 5.2 | 10.1 | 0.0 | 20.8 | 0.0 |
| iso-butylene | 19.6 | 19.5 | 0.0 | 40.0 | 0.0 |
| n-butane | 34.6 | 36.2 | 70.6 | 0.0 | 0.0 |
| iso-butane | 15.2 | 15.1 | 29.4 | 0.0 | 0.0 |
| 2-butanol | 0.0 | 0.0 | 0.0 | 0.0 | 58.6 |
| tert-butanol | 0.0 | 0.0 | 0.0 | 0.0 | 25.1 |
| C-4 Dimers | 0.0 | 0.0 | 0.0 | 0.0 | 16.4 |
| Total | 100.0 | 100.0 | 100.0 | 100.0 | 100.0 |

As can be seen from Table 3, butadiene present in the raffinate stream is converted mainly to 1-butene, 2-butene, iso-butylene, n-butane, and iso-butane within the hydrogenation unit, such that the first process stream is substantially free of butadiene. Substantially free of butadiene as described herein generally refers an amount of butadiene present of 0.1 to 500 parts per million (ppm). Further, as can be seen the stream exiting the hydration unit (Hydration OUT), the fuel additive product comprises 83.7% by weight alcohols, with the remainder comprising C4 dimers.

Example 3

In this example, a trial was conducted using a single hydration reactor. To mimic a configuration having multiple hydration reactors in series, the reactor product was recycled back through the reactor at specified ratios. In this example, Stream 1 corresponded to the raffinate stream 12; Stream 2 corresponded to the first process stream 16; Stream 3 corresponded to the C4 paraffin stream 56; Stream 4 corresponded to the purified C4 olefin stream 39; and Stream 5 corresponded to the purified fuel additive product stream 48. The compositions are given in weight percent. SHU corresponds to the selective hydrogenation unit 14 and hydration corresponds to the hydration unit 42. Mass flow is measured in total weight percent per hour (TPH).

TABLE 4

Composition throughout the process (recycle/feed ratio: 12:1 (mass:mass))

| | Stream | | | | |
|---|---|---|---|---|---|
| | 1 | 2 | 3 | 4 | 5 |
| Components | SHU IN | SHU OUT | C4 paraffins | Hydration IN | Hydration OUT |
| Butadiene | 17.9 | 0.0 | 0.0 | 0.0 | 0.0 |
| 1-butene | 7.5 | 19.1 | 0.0 | 39.3 | 0.0 |
| 2-butene | 5.2 | 10.1 | 0.0 | 20.8 | 0.0 |
| iso-butylene | 19.6 | 19.5 | 0.0 | 40.0 | 0.0 |
| n-butane | 34.6 | 36.2 | 70.6 | 0.0 | 0.0 |
| iso-butane | 15.2 | 15.1 | 29.4 | 0.0 | 0.0 |
| 2-butanol | 0.0 | 0.0 | 0.0 | 0.0 | 58.6 |
| tert-butanol | 0.0 | 0.0 | 0.0 | 0.0 | 20.1 |
| C4 Dimers | 0.0 | 0.0 | 0.0 | 0.0 | 13.6 |
| Di-Sec-butyl ether | 0.0 | 0.0 | 0.0 | 0.0 | 0.4 |
| Di-tert-butyl ether | 0.0 | 0.0 | 0.0 | 0.0 | 0.1 |
| tert-butyl sec-butyl ether | 0.0 | 0.0 | 0.0 | 0.0 | 7.3 |
| Total | 100.0 | 100.0 | 100.0 | 100.0 | 100.0 |

As can be seen from Table 4, butadiene present in the raffinate stream is converted mainly to 1-butene, 2-butene, iso-butylene, n-butane, and iso-butane within the hydrogenation unit, such that the first process stream is substantially free of butadiene. Substantially free of butadiene as described herein generally refers an amount of butadiene present of 0.1 to 500 parts per million (ppm). Further, as can be seen the stream exiting the hydration unit (Hydration OUT), the fuel additive product comprises approximately 78.7% by weight alcohols, with the remainder comprising ethers and C4 dimers.

The methods disclosed herein include(s) at least the following aspects:

Aspect 1: A method of producing a fuel additive, comprising: passing a raffinate stream comprising C4 hydrocarbons through a hydrogenation unit, forming a first process stream; passing the first process stream through an extractive distillation unit, forming a C4 olefin stream; passing the C4 olefin stream through a stripper column, forming a purified C4 olefin stream; and forming the fuel additive by passing the purified C4 olefin stream through a hydration unit.

Aspect 2: The method of Aspect 1, wherein a source of the raffinate stream comprises a catalytic cracking process and/or an olefin production process.

Aspect 3: The method of any of the preceding aspects, wherein the raffinate stream comprises propane, propylene, 1,3-butadiene, 1,2-butadiene, isobutylene, cis butene, trans-2-butene, 1-butene, isobutane, n-butane, or a combination thereof.

Aspect 4: The method of any of the preceding aspects, wherein the extractive distillation unit uses a solvent comprising hydrogenated heterocyclic compounds with 5 to 6 members, preferably, wherein the solvent further comprises nitrogen, oxygen, a carbonyl group, or a combination thereof.

Aspect 5: The method of any of the preceding aspects, wherein the extractive distillation unit uses a solvent comprising morpholine derivatives and/or pyrrolidone derivatives, preferably, wherein the solvent comprises N-methylpyrrolidone, formylpyrrolidine, N-Formylmorpholine, butyrolactone, or a combination thereof.

Aspect 6: The method of any of the preceding aspects, wherein the purified C4 olefin stream comprises 1-butene and 2-butene.

Aspect 7: The method of any of the preceding aspects, wherein greater than or equal to 90% by weight of any butadiene present in the raffinate stream is converted to 1-butene and/or 2-butene within the hydrogenation unit.

Aspect 8: The method of any of the preceding aspects, further comprising adding tertiary butyl catechol and/or hydrogen to the raffinate stream prior to the hydrogenation unit.

Aspect 9: The method of any of the preceding aspects, further comprising withdrawing a C4 paraffin stream from the extractive distillation unit.

Aspect 10: The method of Aspect 9, wherein the C4 paraffin stream comprises n-butane and iso-butane.

Aspect 11: The method of Aspect 9, further comprising introducing the C4 paraffin stream into a plant for the production of methyl tertiary butyl ether.

Aspect 12: The method of any of the preceding aspects, wherein the hydration unit uses an acid catalyst comprising phosphoric acid, a cation exchange resin, sulphonated polystyrene, hypophosphorous acid, polymer resins, niobium oxide, zeolite, or a combination thereof.

Aspect 13: The method of any of the preceding aspects, wherein a temperature within the hydration unit is 30° C. to 250° C. and a pressure within the hydration unit is 500 kiloPascals to 10,000 kiloPascals.

Aspect 14: The method of any of the preceding aspects, wherein the hydration unit comprises an oscillating baffle reactor, a fixed bed reactor, a membrane integrated reactor, or a combination thereof.

Aspect 15: The method of any of the preceding aspects, wherein greater than or equal to 0.10% by weight of any butene present in the purified C4 olefin stream is converted to butanol within the hydration unit; preferably, greater than or equal to 80% by weight.

Aspect 16: The method of any of the preceding aspects, further comprising withdrawing a fuel additive product from the hydration unit, wherein the fuel additive product comprises 1-butanol, 2-butanol, tert-butyl alcohol, di-isobutene, trimethyl-pentane, other C4 dimers, di-isobutyl ether, di-sec-butyl ether, or a combination comprising at least one of the forgoing.

Aspect 17: The method of Aspect 16, wherein the fuel additive product comprises 0.01% to 50% by weight trimethyl-pentane.

Aspect 18: The method of Aspect 16, wherein an octane number of the fuel additive product is greater than or equal to 87 RON or 80 MON.

Aspect 19: The method of Aspect 16, wherein a Reid vapor pressure of the fuel additive product is less than or equal to 55 kiloPascals.

Aspect 20: A method of producing a fuel additive, comprising: passing a raffinate stream comprising C4 hydrocarbons through a hydrogenation unit, forming a first process stream, wherein greater than or equal to 90% by weight of any butadiene present in the raffinate stream is converted to 1-butene and/or 2-butene within the hydrogenation unit; passing the first process stream and a solvent comprising N-methylpyrrolidone, formylpyrrolidine, N-Formylmorpholine, butyrolactone, or a combination thereof through an extractive distillation unit, producing a C4 olefin stream; passing the C4 olefin stream through a stripper column, producing a purified C4 olefin stream; passing the purified C4 olefin stream through a hydration unit, wherein the purified C4 olefin stream is exposed to an acid catalyst comprising phosphoric acid, cation exchange resin, sulphonated polystyrene, hypophosphorous acid, polymer, niobium oxide, zeolite, or a combination thereof in the hydration unit; and withdrawing a C4 alcohol fuel additive product from the hydration unit, wherein the fuel additive product comprises 0.01% to 50% by weight trimethyl-pentane.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like. In a list of alternatively useable species, "a combination thereof" means that the combination can include a combination of at least one element of the list with one or more like elements not named. Also, "at least one of" means that the list is inclusive of each element individually, as well as combinations of two or more elements of the list, and combinations of at least one element of the list with like elements not named.

All cited patents, patent applications, and other references are incorporated herein by reference in their entirety. However, if a term in the present application contradicts or conflicts with a term in the incorporated reference, the term from the present application takes precedence over the conflicting term from the incorporated reference While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method of producing a fuel additive, comprising:
passing a raffinate stream comprising C4 hydrocarbons through a hydrogenation unit, forming a first process stream, wherein at least a portion of butadiene present in the raffinate stream is converted to 1-butene and/or 2-butene within the hydrogenation unit;
passing the first process stream comprising 1-butene and/or 2-butene through an extractive distillation unit, forming a C4 olefin stream comprising a solvent and a C4 paraffin stream;
passing the C4 olefin stream comprising the solvent through a stripper column, forming a purified C4 olefin stream, wherein at least a portion of the solvent is removed from the C4 olefin stream in the stripper column; and
forming the fuel additive comprising 5% to 50% by weight trimethyl-pentane by passing the purified C4 olefin stream through a hydration unit, wherein at least a portion of butene present in the purified C4 olefin stream is converted to butanol within the hydration unit;
wherein greater than or equal to 80% by weight of any butene present in the purified C4 olefin stream is converted to butanol within the hydration unit;
wherein the purified C4 olefin stream comprises less than 1.0% butadiene by weight prior to passing through the hydration unit; and
wherein the purified C4 olefin stream comprises less than 1.0% by weight n-butane and iso-butane prior to passing through the hydration unit.

2. The method of claim 1, wherein a source of the raffinate stream comprises a catalytic cracking process and/or an olefin production process.

3. The method of claim 1, wherein the raffinate stream comprises at least one of propane, propylene, 1,3-butadiene, 1,2-butadiene, isobutylene, cis-2-butene, trans-2-butene, 1-butene, isobutane, or n-butane.

4. The method of claim 1, wherein the extractive distillation unit uses the solvent, the solvent comprising hydrogenated heterocyclic compounds with 5 to 6 members, and wherein the solvent further comprises at least one of nitrogen, oxygen, or a carbonyl group.

5. The method of claim 1, wherein the extractive distillation unit uses the solvent, the solvent comprising morpholine derivatives and/or pyrrolidone derivatives.

6. The method of claim 1, wherein the purified C4 olefin stream comprises 1-butene and 2-butene.

7. The method of claim 1, wherein greater than or equal to 90% by weight of any butadiene present in the raffinate stream is converted to 1-butene and/or 2-butene within the hydrogenation unit.

8. The method of claim 1, further comprising adding tertiary butyl catechol and/or hydrogen to the raffinate stream prior to the hydrogenation unit.

9. The method of claim 1, further comprising withdrawing the C4 paraffin stream from the extractive distillation unit.

10. The process of claim 9, wherein the C4 paraffin stream comprises n-butane and iso-butane; and wherein the purified C4 olefin stream comprises less than 0.0% by weight n-butane and iso-butane prior to passing through the hydration unit.

11. The method of claim 9, further comprising subjecting the C4 paraffin stream to: (i) a de-isobutanizer column to separate n-butane from iso-butane, (ii) an isomerization unit, (iii) a dehydrogenation unit, and (iv) a methyl tertiary butyl ether synthesis unit to produce methyl tertiary butyl ether.

12. The method of claim 1, wherein the hydration unit uses an acid catalyst comprising at least one of phosphoric acid, a cation exchange resin, sulphonated polystyrene, hypophosphorous acid, polymer resins, niobium oxide, or a zeolite.

13. The method of claim 1, wherein a temperature within the hydration unit is 30° C. to 250° C. and a pressure within the hydration unit is 500 kiloPascals to 10,000 kiloPascals.

14. The method of claim 1, wherein the hydration unit comprises at least one of an oscillating baffle reactor, a fixed bed reactor, or a membrane integrated reactor.

15. The method of claim 1, further comprising withdrawing a fuel additive product from the hydration unit, wherein the fuel additive product comprises at least one of 1-butanol, 2-butanol, tert-butyl alcohol, di-isobutene, trimethyl-pentane, other C4 dimers, di-isobutyl ether, or di-sec-butyl ether.

16. The method of claim 15, wherein an octane number of the fuel additive product is greater than or equal to 87 RON or 80 MON.

17. The method of claim 16, wherein a Reid vapor pressure of the fuel additive product is less than or equal to 55 kiloPascals.

18. A method of producing a fuel additive, comprising:
passing a raffinate stream comprising C4 hydrocarbons through a hydrogenation unit, forming a first process stream, wherein greater than or equal to 90% by weight of any butadiene present in the raffinate stream is converted to 1-butene and/or 2-butene within the hydrogenation unit, the hydrogenation unit comprising a first reactor stage, a second reactor stage and a third reactor stage in series;
passing the first process stream comprising 1-butene and/or 2-butene and a solvent comprising at least one of N-methylpyrrolidone, formylpyrrolidine, N-Formylmorpholine, or butyrolactone through an extractive distillation unit, producing a C4 olefin stream and a C4 paraffin stream;
passing the C4 olefin stream comprising the solvent through a stripper column, producing a purified C4 olefin stream, wherein at least a portion of the solvent is removed from the C4 olefin stream in the stripper column;
passing the purified C4 olefin stream through a hydration unit, wherein the purified C4 olefin stream is exposed to an acid catalyst comprising at least one of phosphoric acid, a cation exchange resin, sulphonated polystyrene, hypophosphorous acid, polymer, niobium oxide, or a zeolite, and wherein greater than or equal to 80% by weight of any butene present in the purified C4 olefin stream is converted to butanol within the hydration unit, and wherein the purified C4 olefin stream comprises less than 1.0% butadiene by weight prior to passing through the hydration unit, and wherein the purified C4 olefin stream comprises less than 1.0% by weight n-butane and iso-butane prior to passing through the hydration unit; and withdrawing a C4 alcohol fuel additive product from the hydration unit, wherein the fuel additive product comprises 5% to 50% by weight trimethyl-pentane; and wherein the fuel additive product further comprises at least one of 1-butanol, 2-butanol, tert-butyl alcohol, di-isobutene, other C4 dimers, di-isobutyl ether, or di-sec-butyl ether;

wherein an octane number of the fuel additive product is greater than or equal to 87 RON or 80 MON, and a Reid vapor pressure of the fuel additive product is less than or equal to 55 kiloPascals; and further comprising withdrawing the C4 paraffin stream from the extractive distillation unit, wherein the C4 paraffin stream comprises n-butane and iso-butane, and subjecting the C4 paraffin stream to: (i) a de-isobutanizer column to separate n-butane from iso-butane, (ii) an isomerization unit, (iii) a dehydrogenation unit, and (iv) a methyl tertiary butyl ether synthesis unit to produce methyl tertiary butyl ether; and further comprising withdrawing a recycle stream from the extractive distillation unit and recycling the recycle stream to the raffinate stream or to a steam cracker unit.

\* \* \* \* \*